United States Patent [19]

Dorawala et al.

[11] 4,075,255

[45] Feb. 21, 1978

[54] STEAM DEALKYLATION WITH HYDROGEN TREATED CATALYST OF GROUPS I, VI B, VIII

[75] Inventors: Tansukhlal G. Dorawala, Wappingers Falls; Russell R. Reinhard, Hopewell Junction; John H. Estes, Wappingers Falls, all of N.Y.

[73] Assignee: Texaco Inc., New York, N.Y.

[21] Appl. No.: 717,843

[22] Filed: Aug. 26, 1976

Related U.S. Application Data

[62] Division of Ser. No. 610,198, Sept. 4, 1975, Pat. No. 4,008,181.

[51] Int. Cl.² ............................................. C07C 3/58
[52] U.S. Cl. ............................................. 260/672 R
[58] Field of Search ............................. 252/465, 470; 260/672 R

[56] References Cited

U.S. PATENT DOCUMENTS

| | | | |
|---|---|---|---|
| 3,649,707 | 3/1972 | Lester | 260/672 R |
| 3,700,745 | 10/1972 | Kovach et al. | 260/672 R |
| 3,760,023 | 9/1972 | Patrick et al. | 260/672 R |
| 3,812,196 | 5/1974 | Uchiyama et al. | 260/672 R |

*Primary Examiner*—O. R. Vertiz
*Assistant Examiner*—Brian E. Hearn
*Attorney, Agent, or Firm*—Thomas H. Whaley; Carl G. Ries; Carl G. Seutter

[57] ABSTRACT

Alkylaromatic hydrocarbons are dealkylated with steam in the presence of catalyst (typically containing oxides of nickel, potassium, chromium, and aluminum) which has been hydrogen-treated at high temperature.

8 Claims, No Drawings

STEAM DEALKYLATION WITH HYDROGEN TREATED CATALYST OF GROUPS I, VI B, VIII

This is a division of application Ser. No. 610,198, filed Sept. 4, 1975, now U.S. Pat. No. 4,008,181.

FIELD OF THE INVENTION

This invention relates to the conversion of hydrocarbons. More particularly, it relates to the dealkylation of alkylaromatic hydrocarbons such as toluene in the presence of a catalyst which has been activated at high temperature in the presence of hydrogen.

BACKGROUND OF THE INVENTION

As is well known to those skilled in the art, steam demethylation has commonly been carried out by passing an alkylaromatic hydrocarbon, typically toluene, together with steam through a furnace at high temperatures to yield a product containing principally benzene. Steam dealkylation is carried out in the presence of catalysts; and typical catalyst compositions may include zeolites or amorphous inorganic oxides such as silica, alumina, silica-alumina magnesia, zirconia, etc. commonly bearing metal oxides. It is found however that typical prior art processes are less than fully satisfactory because of low yields of product, degradation of catalyst, poor product selectivity etc. Various prior art techniques have attempted to improve the conversion, yield, or selectivity of the catalyst systems heretofore employed.

It is an object of this invention to provide a steam dealkylation process particularly characterized by use of an active catalyst. Other objects will be apparent to those skilled in the art.

STATEMENT OF THE INVENTION

In accordance with certain of its aspects, the novel process of this invention for preparing a catalyst, characterized by its ability to catalyze steam dealkylation of alkylaromatic hydrocarbons, may comprise treating a calcined supported catalyst bearing oxides of (i) a Group VIII metal, (ii) a Group VI B metal, and (iii) a Group I A metal in the presence of hydrogen for 4-16 hours at 950°-1400° F thereby forming a treated catalyst; and
recovering said treated catalyst.

DESCRIPTION OF THE INVENTION

In accordance with certain of its aspects, the charge alkylaromatic hydrocarbon which may be treated by the process of this invention may be a stream typically having a boiling point of 176°-1292° F (80°-700° C). The stream may contain alkylaromatic hydrocarbons, either pure or in admixture, in varying quantities. This charge stream may typically contain toluene, xylenes, ethyl benzenes, propyl benzenes etc. The preferred charge hydrocarbon contains toluene; and in the preferred embodiment, it may be substantially entirely toluene se.

Typical charge streams which may be treated by the process of this invention may include aromatic extracts or reformate streams containing alkylaromatic hydrocarbons. Illustrative of such charge streams may be a reformate commonly containing the following components (% by volume);

TABLE

| Component | Broad | Typical |
|---|---|---|
| Paraffins | 30-45 | 40 |
| Olefins | 0-2 | 1 |
| Naphthenes | 1-5 | 3 |
| Aromatics | 45-65 | 56 |

Of the aromatic content of the reformate 80-100%, typically 90% may be present as alkylaromatic hydrocarbons.

This reformate may have a (RON Clear) octane number of 90, an IBP of 115° F, an EBP of 410° F, and an API gravity of 47.7.

Particularly desirable results may be achieved by use, as the hydrocarbon charge, of compositions containing substantial proportions of toluene. In a preferred embodiment, the charge may consist essentially of toluene.

The supported catalyst which may be employed in practice of the process of this invention may comprise a catalyst support bearing oxides of (i) a Group VIII metal, (ii) a Group VI B metal and (iii) a Group I A metal.

The Group VIII metal may include iron Fe, cobalt Co, nickel Ni, ruthenium Ru, rhodium Rh, palladium Pd, osmium Os, iridium Ir, and platinum Pt. Preferably the Group VIII metal may be nickel or cobalt; and in the most preferred embodiment, it is nickel.

The Group VI B metal may be chromium Cr, molybdenum Mo, or tungsten W; and in the preferred embodiment, it is chromium Cr.

The Group I A metal, an alkali metal, may be lithium Li, sodium Na, potassium K, rubidium Rb, or caesium Cs. In the preferred embodiment, it is potassium K.

The catalyst support may be active or inactive or inert. Typically the support may be a clay, a silica, a metal oxide, a zeolite, etc. The preferred porous materials may include alumina, silica, silica-alumina, silica-magnesia, silica-titania, silica-beryllia, silica-zirconia, silica-alumina-magnesia, etc. The preferred support is an inert support such as alumina, preferably gamma-alumina.

In typical practice of the process of this invention, the catalyst composition may contain the following components in the indicated parts by weight (expressed as oxide):

TABLE

| Component | Broad | Preferred | Typical |
|---|---|---|---|
| Group VIII | 0.5-40 | 0.5-20 | 15 |
| Group VI B | 0.01-40 | 10-38 | 15 |
| Group I A | 0.01-5 | 1-4 | 2 |
| Support | 15-99.5 | 38-88.5 | 68 |

The preferred catalyst may be that containing nickel-chromium-potassium-aluminum; and the catalyst composition may contain the following (expressed as oxide):

TABLE

| Component | Broad | Preferred | Typical |
|---|---|---|---|
| Ni | 6-40 | 6-20 | 15 |
| Cr | 0.01-40 | 10-38 | 15 |
| K | 0.01-5 | 1-4 | 2 |
| Al | 15-94 | 38-83 | 68 |

In terms of molar proportions, the catalyst may be represented by the formula $$a\,(VIII)_{2/n}O : b\,(VI)_{2/m}O : c\,(I)_2O : d\,(Supp)$$

wherein (VIII) represents a metal of Group VIII of the Periodic Table having a valence $n$, (VI) represents a metal of Group VI B of the Periodic Table having a valence $m$, (I) represents a metal of Group I A of the Periodic Table, and Supp represents the support. $a$ may be 0.002–0.75, preferably 0.002–0.38, say 0.20; $b$ may be 0.0001–0.78, preferably 0.13–0.75, say 0.29; $c$ may be 0.00003–0.17, preferably 0.003–0.13, say 0.02; and $d$ is 0.15–2.49, preferably 0.38–2.21, say 0.68.

In the preferred embodiment, the catalyst may be represented by the formula $a$ NiO:$b$ Cr$_{2/3}$O : $c$ K$_2$O : $d$ (Supp)

wherein $a$ is 0.08–0.54, preferably 0.08–0.27, say 0.20; $b$ is 0.0002–0.78, preferably 0.21–0.75, say 0.29; $c$ is 0.01–0.05 preferably 0.01–0.04, say 0.02; and $d$ is 0.15–2.49, preferably 0.38–2.21, say 0.68.

When the support is alumina, as in the preferred embodiment, the catalyst composition may be represented by the formula $a$ NiO : $b$ Cr$_{2/3}$O : $c$ K$_2$O : $d$ Al$_2$O$_3$ and $d$ may preferably be 0.15–0.93, more preferably 0.38–0.81, say 0.68.

In practice of this invention, the catalyst may be prepared by immersing a catalyst support in a solution containing the metal ions. The support, typically a gamma-alumina extrudate of 1.5 mm diameter and 10 mm length, may first be steam sintered at 900°–1400° F, say 1110° F for 5–25 hours, say 12 hours. During sintering, there may be passed through the bed, air at VHSV of 40–600, say 230 together with steam at water VHSV of 0.05–0.10, say 0.06. The steamed alumina is then calcined for 1–5, say 2 hours at 900°–1200° F, say 1000° F. The initial surface of the alumina, typically 200–400, say 231 meter $^2$/gram may be decreased to 70–95%, say about 90% to a value of 140–380, say 192 meter $^2$/gram.

The support (242 parts), preferably as so treated, is cooled to 32°–80° F, say about 32° F and wetted with 200–2525 parts, say 890 parts of solution prepared by dissolving soluble decomposable salts of metals of Group VIII, VI B, and Group I A in aqueous solution. Preferably 5–1000 parts, more preferably 200–1000, say 792 parts of a salt of a Group VI B metal, typically chromium nitrate nonahydrate Cr (NO$_3$)$_3$.9H$_2$O and 5–25 parts, preferably 10–23, say 17.2 parts of a salt of a Group I A metal, typically potassium nitrate and 50–700, say 267 parts of a salt of a Group VIII metal, typically Ni(NO$_3$)$_2$.6H$_2$O are dissolved in 60–2900 parts, say 343 parts of water to yield total solution in amount of 70–3925 parts, say 1233 parts. (Although nitrates of the metals are preferaby employed, acetates, formates, citrates, or other soluble, decomposable salts may be used).

The solution is poured over the support and is stirred intermittently for 0.5–10 hours, say 1 hour and the solution (50–2400 parts, typically 731 parts) may then be decanted. The impregnated support is dried at 212°–400° F, say 300° F.

Further treatment includes heating for 0.5–24 hours, say 1 hour, at 650°–1000° F, say 700° F in a flowing stream of air to decompose the decomposable salts, typically nitrates, and then calcining for 1–10 hours, say 2 hours at 600°–1000° F, say 700° F to yield 260–1850 parts, say 462 parts having a density of 0.7–1.5, say 1.11.

The product catalyst so prepared may be characterized by the formula $a$ (VIII)$_{2/n}$ O : $b$ (VI)$_{2/m}$O : $c$ (I)$_2$O : $d$ (Supp)

wherein all the symbols are as noted supra.

Preferred catalyst compositions may have the formulae:

0.2 NiO : 0.59 Cr$_{2/3}$O : 0.02 K$_2$O : 0.52 Al$_2$O$_3$ 0.2 NiO : 0.3 Cr$_{2/3}$O : 0.02 K$_2$O : 0.68 Al$_2$O$_3$ 0.17 NiO : 0.65 Cr$_{2/3}$O : 0.02 K$_2$O : 0.48 Al$_2$O$_3$ 0.20 CoO : 0.20 Cr$_{2/3}$O : 0.02 Na$_2$O : 0.34 SiO$_2$

A preferred composition composition may contain 17.7% NiO, 13.2%, Cr$_{2/3}$O, 1.9% K$_2$O, and 61.6% Al$_2$O$_3$. Another preferred composition may contain 11.9% NiO, 30.4% Cr$_{2/3}$O, 1.4% K$_2$O, and 48.2% Al$_2$O$_3$. Another preferred composition may contain 14.2% NiO, 25.1% Cr$_{2/3}$O, 1.8% K$_2$O, and 50.7% Al$_2$O$_3$. The percentages in this paragraph are on a weight basis.

The catalyst composition used in practice of the process of this invention may be prepared by impregnating the support with solutions of metals of Groups VIII, VI B, and I A. Typically for example it may be found that the catalyst may be prepared by:

a. impregnating the support sequentially with several solutions each containing one or more of the metals and thereafter drying and calcining;

b. impregnating the support with one or more solutions containing less than all of the metals (i.e. species or amount), drying and/or calcining, thereafter impregnating the support with the remaining metals, and drying and/or calcining; etc.

It is unexpectedly found however that substantially superior results are achieved (in terms of conversion, yield, and/or selectivity) if the Group VI B and I A metals are impregnated, dried and calcined on the catalyst support prior to the impregnation thereof with the Group VIII metal.

In the preferred embodiment, the catalyst support may thus be prepared by impregnating the support, typically alumina, with one solution containing soluble decomposable salts of the Group VI B and Group I A metals, typically chromium and potassium, drying and calcining, thereafter impregnating the so-obtained pre-catalyst with a solution of a soluble decomposable salt of the Group VIII metal, typically nickel, and drying and calcining. Catalysts containing the after-deposited Group VIII metal (i.e. the Group VIII metal deposited after the Group VI B and Group I A metals are present with the support) and particularly characterized by high yields of dealkylated product. Preferably at least a portion of the Group VIII metal (more preferably a major portion i.e. greater than 50%) is afterdeposited.

In the preferred embodiment, the catalyst composition may be in the form of pellets, cylinders, or randomly shaped particles; a typical catalyst composition may be in the form of cylinders, of diameter 1–15 mm, say 1.5 mm and height 1–15 mm, say 8–10 mm.

It is a feature of this invention that improved results (particularly in terms of increased conversion and yield - at desirably high selectivity) may be achieved by treating the calcined supported catalyst for 4–16 hours, preferably 4–8 hours, say 6 hours in the presence of hydrogen. Treating is effected at high temperature — i.e. at a temperature above that at which the subsequent steam dealkylation reaction is normally carried out. Although some improvement may be obtained by treating at a temperature within the normal steam dealkylation range (e.g. 600°-950° F), it is preferred that treating be carried out at a temperature above that of the normal stream dealkylation. The preferred temperature at which treating is preferably carried out is 950°-1400° F, more preferably 1000°-1250° F, say 1200° F. Preferably hydrogen treating by the process of this invention may be carried out at temperatures which are 150°-600° F, say 450° F higher than those of subsequent steam dealkylation.

Treating of the calcined supported steam dealkylation catalyst of this invention may preferably be carried out after the catalyst is in place in the reaction vessel. The vessel may be filled with catalyst composition to a bulk density of 50-80 pcf, say 70 pcf. In the treating operation, the catalyst composition is heated to 950°-1400° F, preferably 1000°-1250° F, say 1200° F in the presence of a reducing gas containing at least about 30 mole % hydrogen. The gas will preferably be substantially free of active components (other than hydrogen) which are capable of reacting with any of the materials in the system. It is particularly desirable that the gas be free of oxidizing components including oxygen.

The gas may contain (in addition to hydrogen) inert gases such as helium or more preferably light paraffins such as methane, ethane, propane, etc. Hydrogen may be present typically in amount of 30-100 mole %, preferably 80-100 mole %, say 100 mole %; i.e. the preferred embodiment may be that in which the gas consists essentially of hydrogen.

Preferably the catalyst composition may be maintained for 4-16 hours, typically 4-8 hours, say 6 hours in a stream of flowing hydrogen typically flowing at a space velocity VHSV (STP) greater than about 3, more preferably greater than 40, say 40-500, typically 95.

When treating is carried out at atmospheric pressure, as in the preferred embodiment, the partial pressure of hydrogen may be at least about 9 psig (400 mm Hg), preferably 12-15 psia, say 15 psia (760 mm Hg).

Post treating cooling is typically carried out by maintaining the activated catalyst in a stream of flowing steam for 1-10 hours, preferably 1-5 hours, say 2 hours as the temperature is lowered to the steam dealkylation temperature of 600°-950° F, preferably 650°-900° F, say 800° F. Preferably steam is present during post-activation in amount of 50-100 mole %, typically 80-100 mole %, say about 100 mole % of the flowing stream.

It is entirely unexpected that the high temperature hydrogen treatment, as carried out in practice of the process of this invention, would effect any desirable change in the nature of the catalyst because one would expect that, at the high temperatures employed, the catalyst would be harmed i.e. that undesirable structural changes in the catalyst structure would occur which would decrease the structural strength and the activity of the catalyst.

It is a feature of the novel catalyst of this invention that it may be employed in hydrocarbon conversion processes, typified by dealkylation of alkylaromatic hydrocarbons, with the attainment of unexpected results. Among these may be noted an increase in conversion and yield at a high level of selectivity.

In the preferred embodiment, steam dealkylation of an alkylaromatic hydrocarbon charge may be carried out by passing the charge at 600°-950° F, preferably 650°-900° F, say 800° F and pressure of 0-400 psig, preferably 0-200 psig, say 0 psig together with steam in amount of 2-25 moles, preferably 3-15 moles, say 6 moles per mole of hydrocarbon charge (corresponding to 100-1250%, preferably 150-750%, say 300% of the stoichiometric quantity) to a reaction zone. In commercial practice it may be desirable to operate at e.g. 125 psig.

During steam dealkylation at these conditions, alkyl groups are removed from the charge alkylaromatic hydrocarbons to form product hydrocarbons bearing lesser numbers of alkyl groups on the aromatic nuclei. When the charge hydrocarbon contains ethylbenzenes for example, the product stream may contain dealkylated products including benzene. When the charge hydrocarbon contains xylenes, the product stream may contain toluene, benzene, etc. When the charge hydrocarbon stream contains toluene, as in the preferred embodiment, the product hydrocarbon stream may contain benzene. In addition, the product hydrocarbon stream may contain the paraffin derived from the charge e.g. ethane or methane; and it may contain unreacted charge hydrocarbons in addition to other by-products.

Product hydrocarbon may be withdrawn from the reaction vessel and condensed. The liquid condensate may represent a recovery of 50-94 mole %, preferably 70-94 mole %, say 85 mole % of the hydrocarbon charged.

In the case of a pure toluene charge for example, the product (moles per 100 moles of charge toluene) may contain the following:

TABLE

| Component | Broad | Preferred | Typical |
|---|---|---|---|
| Unreacted toluene | 4-79 | 13-70 | 19 |
| benzene | 20-70 | 30-70 | 61 |
| hydrogen | 60-183 | 90-180 | 165 |
| $CO_2$ | 20-61 | 30-60 | 55 |

In practice of the process of this invention according to the one embodiment, the reaction is carried out on a short cycle basis; i.e. the reaction proper (with a charge of steam and hydrocarbon) is carried out for 0.5-3.0 minutes, preferably 0.5-2.0 minutes, say 1 minute and then the catalyst is regenerated by shutting off the flow of hydrocarbon (and contacting it with the hydrocarbon-free steam) for 1.5-9.0 minutes, preferably 1.5-6 minutes, say 3 minutes. The ratio of regeneration time to reaction time may be 1-5, preferably 2-4, say 3.

It is found during practice of the process of this invention that it is possible to achieve improved catalyst activity. For example the toluene conversion (in terms of mole percent of toluene charge converted) may be 50-95%, typically 75-90%, say 84% in the preferred embodiment in contrast to comparable processes wherein the corresponding values are less than 45%.

It is also a feature of the process of this invention in its preferred embodiment that it permits attainment of benzene yield (in terms of mole percent of the charge toluene converted to benzene) which may be 40-70%, typically 50-60%, say 59%. Comparable processes may achieve benzene yields of less than about 50% and commonly as low as 5-20%.

The novel process permits attainment of these conversions and yields with a high selectivity. The selectivity (in terms of mole percent of benzene in the product hydrocarbon stream) may approach 95% and may commonly be 65-90%.

DESCRIPTION OF THE PREFERRED EMBODIMENTS

Practice of the process of this invention will be apparent to those skilled in the art from the following illustrative embodiments wherein, as elsewhere in this description, all parts are parts by weight unless otherwise specifically stated.

EXAMPLE I

In this control example, a catalyst is to be prepared corresponding to the formula

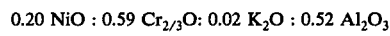

0.20 NiO : 0.59 $Cr_{2/3}O$ : 0.02 $K_2O$ : 0.52 $Al_2O_3$

The catalyst support is gamma-alumina in the form of cylinders of average height 10 mm and diameter 1.5 mm (Aero 100 brand product of American Cyanamid) and it possesses a surface area of 231 square meters per gram. The support is steam sintered in a stainless steel tubular reactor by heating to 1110° F for 12 hours while in contact with a moving stream containing 64 g/hr of water and 8.0 cubic feet per hour of air. After 12 hours, the steam is shut off and the alumina is calcined at 1000° F for 2 hours in a stream of air (8.0 cubic feet per hour). The surface area of the calcined alumina is 192 m$^2$/g.

318 parts of this calcined alumina is placed with a container and chilled to 32° F. The chilled alumina is wetted with an aliquot (400 parts) of a solution prepared by dissolving 446 parts of nickelous nitrate hexahydrate $Ni(NO_3)_2.6H_2O$, 950 parts of chromium nitrate nonahydrate $Cr(NO_3)_3.9H_2O$, and 25.7 parts of potassium nitrate $KNO_3$ in 150 parts of water — yielding 1100 parts of total solution. The so-wetted support is dried at 300° F for 2 hours, the nitrates decomposed at 700° F, and the support then calcined for 2 hours at 1000° F. The dry material is subjected to the same sequence again to absorb the entire solution onto the support. The final product, after the second calcining at 700° F (to decompose the nitrates) is further calcined for 2 hours at 1000° F to yield 582 parts of control catalyst.

The catalyst actually corresponds to

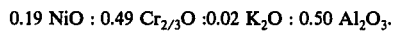

0.19 NiO : 0.49 $Cr_{2/3}O$ : 0.02 $K_2O$ : 0.50 $Al_2O_3$.

In this control example, the catalyst is reduced in flowing hydrogen (2 cubic feet per hour) at 750° F for 4 hours.

EXAMPLE II

In this control Example, 159 parts of the catalyst of Example I is charged to a Vycor tube and treated with flowing hydrogen (0.5 cubic feet per hour) at 900° F for 4 hours. This reduced catalyst is then charged into a steel reactor and pressured with 500 psig of carbon monoxide. The reactor is heated to 140° F and allowed to stand for two hours during which time the pressure drops to 470 psig.

The reactor is heated to 400° F and then depressured rapidly. The catalyst is cooled to 25° C in flowing nitrogen (0.5 cubic feet per hour); and 149 parts of catalyst are recovered.

EXAMPLE III

In this experimental example, carried out in accordance with practice of the process of this invention, 161 parts of the catalyst prepared in Example I is charged to a tubular reactor and treated with flowing hydrogen (0.5 cubic feet per hour) at 1200° F for six hours. Product experimental catalyst is recovered in amount of 155 parts.

EXAMPLE IV-XVII

In each of these comparative examples, 100 ml of catalyst is charged to a fixed bed tubular reactor (2.5 cm diameter × 46 cm long vertically mounted with inlet at top). The catalyst is centered in the reactor by Berl saddles (6 mm). Activation is effected by heating to 900° F in the presence of flowing (one liter per minute) hydrogen, holding at 900° F for 14–16 hours in 0.5 liters per minute of hydrogen, and then holding at 900° F for 2 hours in 35 g./hr. of steam plus 0.5 liters per minute of hydrogen. At the end of this period, the hydrogen flow is turned off; and the reactor temperature is lowered to 650° F in the presence of steam alone.

At this time the toluene pump was turned on and the data noted in the following table were taken on a short cycle basis. This is effected by a 1.0 minute reaction period during which steam and toluene are charged followed by a 3 minute regeneration period during which steam alone is charged. In each instance a preliminary period of 30 minutes is allowed to pass; and the product is collected over 45 minutes.

There are tabulated in the following Table the average temperature ° F of the catalyst bed, the weight hourly space velocity WHSV of the toluene charged, the mole ratio of steam to toluene, the toluene conversion (in terms of mole % of charge converted), the benzene yield (in terms of mole percent of charge converted to benzene), and benzene selectivity (in terms of moles of benzene recovered in the products per one hundred moles of toluene converted in the reaction.)

In these Examples the catalyst of Example I is used in control Examples IV-VII; the catalyst of Example II is used to control Examples VIII-XII; and the experimental catalyst of Example III is used in experimental Examples XIII-XVII.

TABLE

| Example | IV* | V* | VI* | VII* | VIII* | IX* | X* | XI* | XII* | XIII | XIV | XV | XVI | XVII |
|---|---|---|---|---|---|---|---|---|---|---|---|---|---|---|
| Temp. ° F | 650 | 725 | 800 | 875 | 645 | 735 | 800 | 875 | 950 | 650 | 725 | 800 | 875 | 800 |
| Toluene WHSV | 0.19 | 0.20 | 0.20 | 0.20 | 0.18 | 0.18 | 0.19 | 0.18 | 0.19 | 0.13 | 0.14 | 0.15 | 0.15 | 0.18 |
| St:Tol Mol Ratio | 11.1 | 10.8 | 16.6 | 10.8 | 11.1 | 9.6 | 8.7 | 9.2 | 8.7 | 14.7 | 11.8 | 10.5 | 10.5 | 9.2 |
| Tol Conv. Mol % Chg | 7.0 | 14.7 | 38.1 | 53.6 | 0.5 | 0.8 | 1.7 | 2.0 | 3.2 | 39.5 | 71.1 | 84.3 | 89.1 | 81.2 |
| Benzene Yield Mol % Chg | 6.9 | 16.0 | 34.5 | 49.5 | 0.3 | 0.7 | 1.5 | 1.7 | 3.1 | 36.4 | 59.1 | 58.8 | 45.3 | 61.0 |
| Benzene Selectivity % | 98.6 | 108.8 | 90.6 | 92.4 | 60.0 | 87.5 | 88.2 | 85.0 | 96.9 | 92.1 | 83.1 | 69.7 | 50.8 | 75.1 |

*Control examples

From the above table, it is apparent that use of the novel of this invention, as shown in Examples XIII-X-

VII, permits attainment of results which are unexpectedly superior to those achieved by control Examples IV-XII. By way of illustration, the conversion, yield, and selectivity of experimental Example XIII (run at 650° F) are each slightly higher than the corresponding values of control VI (run at 800° F).

Experimental Example XV (run at 800° F) shows that an improvement of 70% (i.e. 58.8% v 34.5%) in benzene yield may be achieved by the process of this invention.

Generally it may be observed that practice of the process of this invention may permit attainment of the following unexpected results:

a. At a given temperature, the toluene conversion and the benzene yield may be increased;
b. Higher conversion or yield may be achieved at desirably lower temperature; and
c. Across the entire range of operating temperature, the benzene yield is desirably high.

It is a particular feature of the novel catalyst of this invention that the catalyst may be prepared by the addition, to the support, of metals of Groups VIII, VI B, and I A; and the Group VIII metal, typically nickel, may be added before the others, with the others, or after the other metals have been deposited.

Although this invention has been illustrated by reference to specific embodiments, it will be apparent to those skilled in the art that various changes and modifications may be made whfich clearly fall within the scope of this invention.

We claim:

1. The process for dealkylating an alkylaromatic hydrocarbon which comprises
   a. treating a calcined supported catalyst bearing oxides of (i) a Group VIII metal, (ii) A group VI B metal, and (iii) a Group I A metal in the presence of hydrogen for 4-16 hours at 950°-1400° F thereby forming a treated catalyst;
   b. passing a mixture of steam and alkylaromatic hydrocarbon, at steam dealkylating conditions, into contact with said treated catalyst thereby forming a product gas containing dealkylated alkylaromatic hydrocarbons; and
   c. recovering said dealkylated alkylaromatic hydrocarbon.

2. The process for dealkylating an alkylaromatic hydrocarbon as claimed in claim 1 wherein said Group VIII metal is nickel or cobalt.

3. The process for dealkylating an alkylaromatic hydrocarbon as claimed in claim 1 wherein said Group VIII metal is nickel.

4. The process for dealkylating an alkylaromatic hydrocarbon as claimed in claim 1 wherein said Group VI B metal is chromium.

5. The process for dealkylating an alkylaromatic hydrocarbon as claimed in claim 1 wherein said Group I A metal is potassium.

6. The process for dealkylating an alkylaromatic hydrocarbon as claimed in claim 1 wherein said support contains alumina.

7. The process for dealkylating an alkylaromatic hydrocarbon as claimed in claim 16 wherein said catalyst has the formula $$a\ (VIII)_{2/n} O : b\ (VI)_{2/m} O : c\ (I)_2O : d\ (Supp)$$

wherein (VIII) represents a metal of Group VIII of the periodic table of valence $n$, (VI) represents a metal of Group VI B of the periodic table of valence $m$, (I) represents a metal of Group I A of the Periodic Table, $a$ is 0.08-0.54, $b$ is 0.0002-0.78, $c$ is 0.01-0.05, $d$ is 0.15-2.49, and (Supp) represents the support.

8. The process for steam demethylating toluene which comprises
   a. treating a calcined supported catalyst having the formula $$(0.08-0.27)NiO:(0.21-0.75)Cr_{2/3}O:(0.01-0.04)K_2O :(0.38-0.81)\ Al_2O_3$$

in the presence of hydrogen for 4-8 hours at 950°-1400° F thereby forming a treated catalyst;
   b. passing a mixture of steam and toluene at 600°-950° F into contact with said treated catalyst thereby forming a product gas containing benzene; and
   c. recovering said product gas containing benzene.

* * * * *